(12) United States Patent
Radford et al.

(10) Patent No.: US 8,167,858 B2
(45) Date of Patent: May 1, 2012

(54) MEDICAL WASTE DISPOSAL SYSTEM ASSEMBLY

(75) Inventors: Richard Radford, Auburn, WA (US); Drew Radford, Seattle, WA (US); Jack Howard, Bothell, WA (US); Wayne Willich, Sun Valley, ID (US)

(73) Assignee: Biofluid Technologies, LLC, Auburn, WA (US)

( * ) Notice: Subject to any disclaimer, the term of this patent is extended or adjusted under 35 U.S.C. 154(b) by 596 days.

(21) Appl. No.: 11/190,217

(22) Filed: Jul. 26, 2005

(65) Prior Publication Data

US 2007/0027432 A1      Feb. 1, 2007

(51) Int. Cl.
*A61M 1/00*      (2006.01)

(52) U.S. Cl. ......... 604/321; 604/540; 604/319; 604/322

(58) Field of Classification Search .................. 604/317, 604/319, 321, 322, 326, 540; 251/25, 213, 251/129.11, 129.14, 129.15, 315.01; 215/307, 215/311, 312, DIG. 3; 588/249, 260
See application file for complete search history.

(56) References Cited

U.S. PATENT DOCUMENTS

| | | | | |
|---|---|---|---|---|
| 4,512,484 A | * | 4/1985 | Mar | 215/221 |
| 4,957,491 A | * | 9/1990 | Parker | 604/317 |
| 5,025,806 A | | 6/1991 | Palmer et al. | |
| 5,195,995 A | * | 3/1993 | Walker | 604/319 |
| 5,224,615 A | * | 7/1993 | Hickerson | 215/218 |
| 5,256,159 A | * | 10/1993 | Newman | 604/317 |
| 5,265,751 A | * | 11/1993 | Lima et al. | 220/288 |
| 5,419,347 A | * | 5/1995 | Carruth | 134/57 R |
| 5,465,841 A | * | 11/1995 | Wilson et al. | 206/366 |
| 5,637,103 A | * | 6/1997 | Kerwin et al. | 604/317 |
| 5,741,237 A | * | 4/1998 | Walker | 604/317 |
| 5,752,612 A | * | 5/1998 | Fritzsche et al. | 215/301 |
| 5,914,047 A | * | 6/1999 | Griffiths | 210/739 |
| 6,027,490 A | * | 2/2000 | Radford et al. | 604/540 |
| 6,176,381 B1 | * | 1/2001 | Mader | 215/219 |
| 6,180,000 B1 | * | 1/2001 | Wilbur et al. | 210/85 |
| 6,367,639 B1 | * | 4/2002 | Mar | 215/213 |
| 6,600,418 B2 | * | 7/2003 | Francis et al. | 340/572.1 |
| 6,712,561 B1 | * | 3/2004 | Valerino et al. | 406/197 |
| 7,273,585 B1 | * | 9/2007 | White | 422/28 |
| 7,525,430 B2 | * | 4/2009 | Nakamura et al. | 340/572.1 |
| 7,556,169 B2 | * | 7/2009 | Cooper et al. | 220/326 |
| 2002/0188259 A1 | * | 12/2002 | Hickle et al. | 604/189 |
| 2002/0196150 A1 | * | 12/2002 | Wildman | 340/573.1 |
| 2004/0204693 A1 | * | 10/2004 | Anderson et al. | 604/319 |
| 2004/0207865 A1 | * | 10/2004 | Wachter et al. | 358/1.15 |
| 2004/0250004 A1 | * | 12/2004 | Wildman | 710/116 |
| 2005/0009122 A1 | * | 1/2005 | Whelan et al. | 435/7.32 |

(Continued)

OTHER PUBLICATIONS

First dictionary definition of "lock" accessed Friday, Mar. 11, 2011 http://dictionary.reference.com/browse/lock.*

(Continued)

*Primary Examiner* — Leslie Deak
(74) *Attorney, Agent, or Firm* — Dwayne E. Rogge; Schacht Law Office, Inc.

(57) ABSTRACT

A novel collection device for collection, storage and disposal of biological products, in conjunction with an improved cleansing method. Disclosed is an apparatus which includes a locking closing member handle to allow for safe transport and disposal of medical waste. Closing member allows for secure containment of medical waste and subsequent apparatus cleaning. Closing member design includes a gap between closing member and housing which facilitates device cleaning after waste disposal.

12 Claims, 8 Drawing Sheets

U.S. PATENT DOCUMENTS

| | | |
|---|---|---|
| 2005/0065640 A1* | 3/2005 | Mallett et al. .................. 700/224 |
| 2005/0065820 A1* | 3/2005 | Mallett et al. ...................... 705/2 |
| 2005/0187529 A1* | 8/2005 | Reasoner et al. ............. 604/317 |
| 2006/0043177 A1* | 3/2006 | Nycz et al. .................... 235/385 |
| 2006/0170551 A1* | 8/2006 | Nakamura et al. ......... 340/572.1 |
| 2006/0181423 A1* | 8/2006 | Bleckmann et al. ....... 340/572.8 |
| 2006/0217993 A1* | 9/2006 | Anderson ......................... 705/1 |
| 2007/0021944 A1* | 1/2007 | Levy .............................. 702/188 |
| 2007/0108946 A1* | 5/2007 | Yamauchi et al. ............ 320/132 |
| 2007/0124009 A1* | 5/2007 | Bradley et al. .................. 700/99 |

OTHER PUBLICATIONS

Second dictionary definition of "lock" accessed Friday, Mar. 11, 2011 http://education.yahoo.com/reference/dictionary/entry/lock.*

* cited by examiner

MEDICAL WASTE DISPOSAL SYSTEM ASSEMBLY

TECHNICAL FIELD

The present invention relates to the storage and disposal of biological waste materials. More particularly, the present invention relates to modular containment devices which provide for controlled collection of biological waste materials. Even more particularly, the present invention relates to modular containment devices which guard against undesired spillage while allowing for automated cleaning of the assembly as well as the containment vessel.

BACKGROUND ART

Safe and economical handling of medical waste faces a number of hurdles. Devices for containment of medical waste must withstand a wide range of temperatures, pH variations, positive and negative pressure forces, and chemical degradation from exposure to complex organic molecules. Medical waste is rarely homogenous, with liquid waste containing solid matter and generating gaseous byproducts. Secure containment of the same requires addressing all of the above concerns.

Modular medical waste disposal systems help address this need, but can still expose health care workers to risks during disposal of the waste and cleaning of the container. Consequently, there has been a long felt need for a device to aid storage and automate waste disposal of medical waste and provide for better container cleaning. Such an improved device would improve health care worker safety and help reduce exposure to hazardous organic materials. Medical waste disposal systems such as those disclosed in U.S. Pat. Nos. 6,027,490 and 6,488,675 are hereby incorporated by reference.

DISCLOSURE OF THE INVENTION

Accordingly, the claimed invention provides an apparatus for containment of biological waste materials with improved storage, handling, disposal and cleaning characteristics. The claimed invention includes an assembly which is seated atop a vessel for biological waste storage. The assembly allows for passage of biological materials into the vessel, and also includes a manual control and closing member to seal the vessel for transportation to a waste disposal station.

To improve health care worker safety, the assembly guards against unintended waste spillage through the inclusion of a closing member operated by a knob which is automatically locked when turned to the 'closed' position. Consequently, the assembly must be manually unlocked in order for the vessel to be emptied of its contents. Quick entry and release grooves incorporated into the top of the assembly allow for sealed connection to a waste disposal device, which can detect closing member pressure and position due to the incorporation of a magnet into the lock release button. Button position can be derived from magnetic or other sensors located on a biofluid disposal station, and are derived by the position of the assembly relative to the disposal device. To improve operator efficiency and versatility of the system a sensor feature is incorporated into the assembly/vessel structure and the wash disposal station. Magnetic or RF signals located on the vessel assembly instruct the disposal station of the appropriate process of data collection.

Improved handling of biological materials creates additional structural considerations in apparatus design. Health care worker safety is improved by making the assembly shatter resistant as well as leak resistant. Devices for containment of biological materials such as medical waste must withstand a wide range of handling abuses in use and transport and temperatures and pressure ranges since collection and cleansing are likely to occur at substantially different positive and negative atmospheric pressures. Complex organic molecules impact on their surroundings with pH variations, and the assembly must be resistant to chemical degradation from exposure to complex organic molecules. Composition of the assembly and its inner workings must take into account all of these concerns.

Apparatus component layout also has resulted in operational improvements over previous devices. Connection of the apparatus to a waste removal station is facilitated through quick attachment and release grooves, which provide a sealed discharge path to a mated receiving chamber adapter to safely discharge vessel contents. To improve working efficiency and reliability the apparatus has been designed with a minimum of gaskets and pivot points. The two-point mounting design for the closing member allows for operational simplicity while providing for controlled engagement of the gaskets. Biological material disposal is improved due to the radiused lumen entry port of the closing member which reduces 'stiction' and enables the low torque required for closing member opening and closing. The adjustable closing member seating ring is threaded and allows for compression adjustment of the closing member and gaskets based upon the number of revolutions the closing member seating ring has been inserted into the apparatus housing. The apparatus housing internal chamber has a larger volume and internal dimensions than the apparatus closing member. This expanded chamber coupled with the flattened ball surface to access and direct cleaning fluids to enter the internal chamber of the housing and two-point closing member pivot mounting approach allows for cleaning fluid to access all internal housing and closing member surfaces. As a consequence, apparatus reliability is high and cleaning of apparatus internal components is optimized.

Finally, medical waste is rarely homogenous, with liquid waste containing solid matter and generating gaseous byproducts. Consequently, the claimed invention provides for enhanced device cleansing through the introduction of a gap between the closing member system and external assembly, allowing for improved automatic cleaning of the assembly after the vessel has been emptied.

BRIEF DESCRIPTION OF THE DRAWINGS

For a better understanding of the present invention, reference is made to the accompanying drawings numbered below. Commonly used reference numbers identify the same or equivalent parts of the claimed invention throughout the several figures.

MODES FOR CARRYING OUT THE INVENTION

Figure 1:
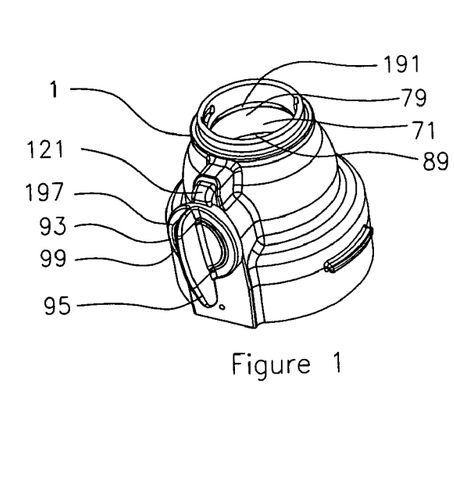
FIG. 1 is a top perspective view of the assembled apparatus.

FIG. 1 is a perspective view of the assembled apparatus. When assembled, housing 1 can be seen with closing member handle 93 and button 121. Since closing member handle is turned to the unlocked and open position, closing member 71 can be seen with angled opening portion 79 of the lumen radiused to facilitate passage of waste (not shown) and subsequent cleaning, straight portion 89 and gap 191 between housing 1 and closing member 71, allowing for greater surface area cleansing of closing member 71 and related parts. The external surface of closing member handle 93 is made up of handle 95 connected to handle face 197 with handle face raised feature 99.

Figure 2:
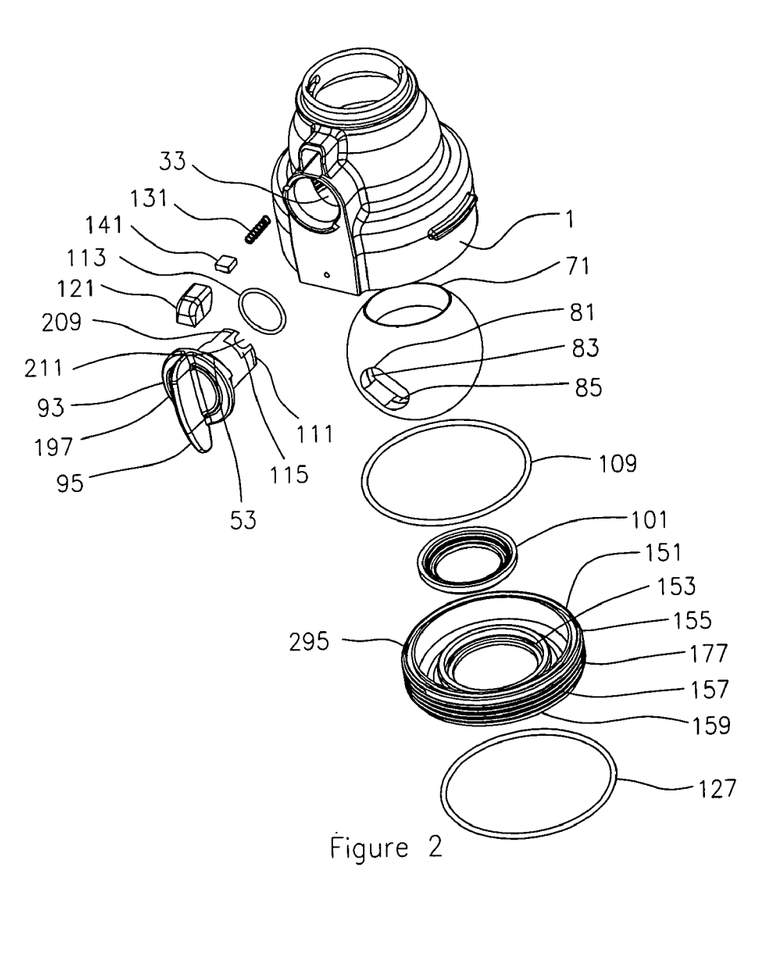
FIG. 2 is an exploded view of apparatus.

FIG. 2 is an exploded view of the apparatus and details of the component parts. Starting with the top of the Figure, housing 1 is shown above closing member 71, closing member seal 101 and upper closing member gasket 109, lower closing member gasket 127, all of which seat into closing member seating ring 151. Depicted across from housing 1 is closing member handle 93, closing member handle gasket 113, handle locking button 121, spring 131 and magnet 141. Closing member seating ring 151 is used to secure closing member 71 to housing 1. Leakage from closing member 71 at the vessel end is prevented by gaskets 109, 127 and closing member seal 101. Closing member handle gasket 113 seats into closing member handle gasket seat 53 to prevent ingress and egress of collected biological material (not shown). Upper closing member gasket 109 seats into upper closing member gasket seat 295, lower closing member seal seats into lower closing member seat 177 and closing member seal 101 seats into closing member seal seat 153 to prevent ingress and egress of collected biological material (not shown). Gasket 109, 113, 127 and seal 101 are made out of suitable material to minimize thermal or pH degradation during operation of the apparatus while providing consistent sealing properties between the closing member 71 and housing 1 over time. In addition to providing orientation indentations for closing member gasket 109 and closing member seal 101, closing member seating ring 151 is threaded 155, concave and contains two tightening facilitator bumps 157, 159 on the opposite side of closing member seal seat 153. Closing member seal 101 is made out of suitable material to minimize thermal or pH degradation during operation of the apparatus while providing consistent sealing properties between the closing member 71 and housing 1 over time. During assembly, closing member handle 93 is press fitted into closing member handle orifice 81 to provide for manipulation of closing member 71. Closing member handle 93 is also designed to slightly flex during assembly with closing member 71 through housing 1 handle orifice 33. Closing member handle 93 has a handle 95 for manipulation of closing member 71. Range of motion of closing member handle 93 is determined by the closing member stop (not shown) and angled closing member stop (not shown) opposite handle face 197. Both function in cooperation with reciprocal notched facets of housing 1. Closing member handle 93 includes closing member handle gasket seat (not shown) to seat closing member handle gasket 113 to prevent ingress and egress of collected biological material (not shown). Closing member handle shaft 103 in one variant is hollow and terminates with closing member handle shaft locking tabs 209, 111 as well as a pair of notches 115, (not shown) to reduce the opposite end of closing member handle 93 from a round conformation to an oblong one. The straight, parallel sides at the non-handle end of closing member handle 93 allow for closing member handle 93 to impart a rotational force on closing member 71. This is possible when closing member handle 93 is seated into closing member 71 at the closing member concave indentation 81. Closing member concave indentation 81 also includes two pockets 83, 85 for seating the closing member shaft locking tabs 209, 111. To provide for additional rotational purchase, closing member handle 93 terminates with the 'u shaped' member 211 and allows for installation of closing member handle 93 into concave indentation 81.

Figure 3:
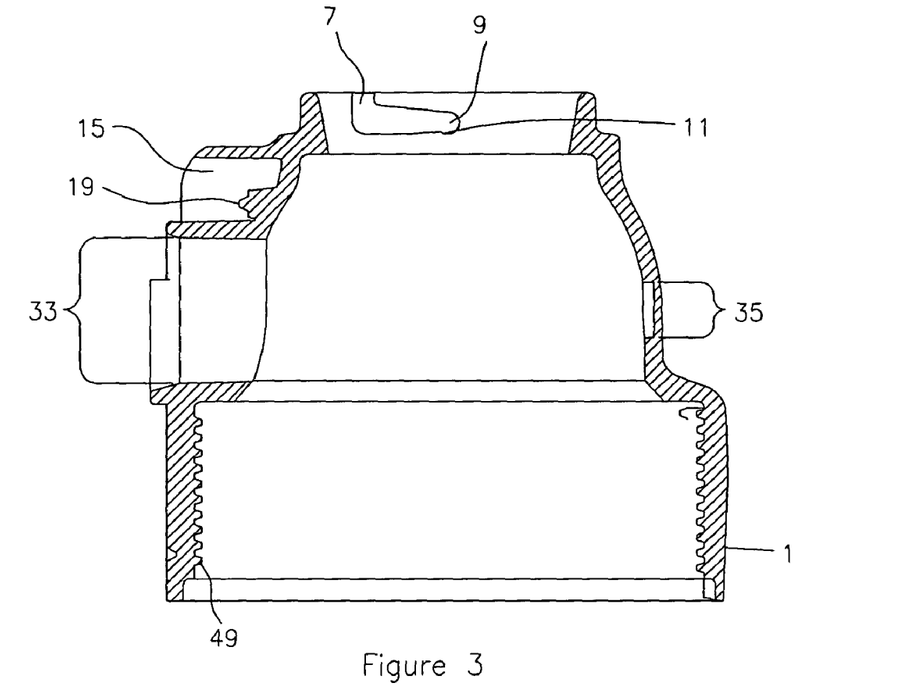
FIG. 3 is a top elevated perspective section view of housing.

FIG. 3 is a top elevated perspective section view of housing 1. Housing 1 provides a ridge 11 to support waste removal. Connection with a collection or removal device (not shown) is achieved through the insertion and rotation of the apparatus along the receptacle neck grooves 7 until rotation is no longer possible and housing 1 is secured into position by receptacle neck groove stop locks 9. Button indentation 15 surrounds spring position post 19. Placement of closing member (not shown) is determined by rotation pin indentation 35, which is centered across from handle orifice 33. Inside housing 1, threaded grooves 49 provide for insertion and tightening equivalently threaded articles.

Figure 4:
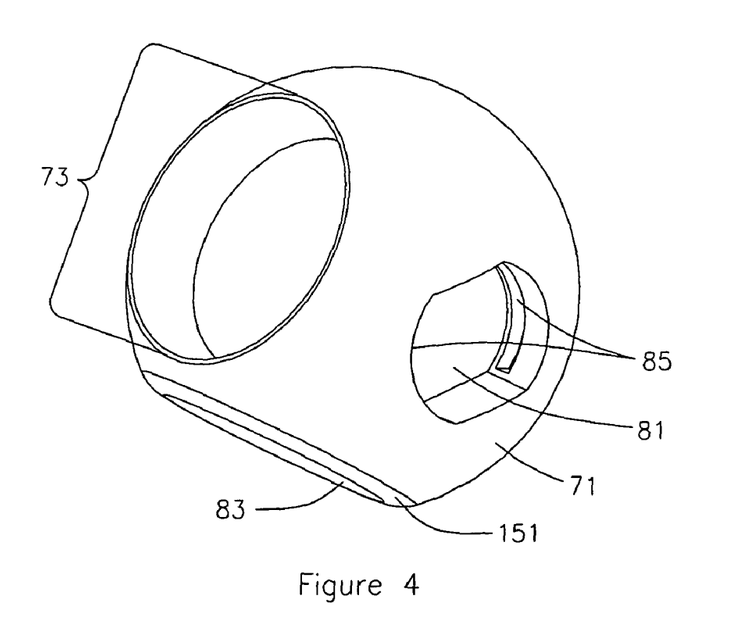
FIG. 4 is a top perspective view of closing member.

FIG. 4 is a top perspective view of closing member 71. Closing member 71 is substantially spherical, yet includes a lumened cylindrical waste passage 73. Also shown is the substantially oblong closing member concave indentation 81 for receiving closing member handle (not shown) which seats onto closing member locking tab indentations 85. Closing member 71 has a flat face 83 which is rotated into position during closing member operation, where the surface of flat face 83 meets the spherical surface of closing member 71 is a radiused surface 151 which assists in directing the cleaning fluid entering the housing chamber 1.

Figure 5:
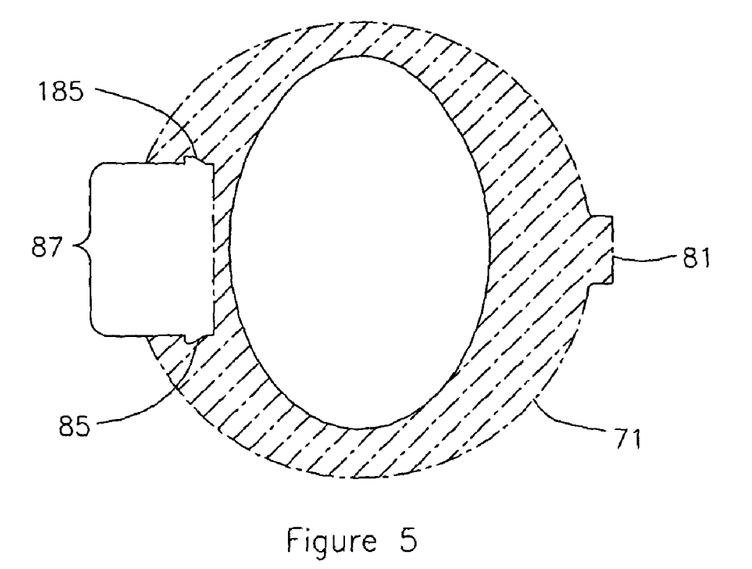
FIG. 5 is a top elevated perspective section view of closing member.

FIG. 5 is a top elevated perspective section view of closing member 71. Rotation pin 81 is cylindrical and allows for seating of the closing member and turning on a single axis. Opposite rotation pin 81 is a substantially oblong closing member concave indentation 87 for receiving closing member handle (not shown) which is locked into position by closing member handle shaft locking tabs (not shown) which seat into closing member locking tab indentations 85, 185.

Figure 6:
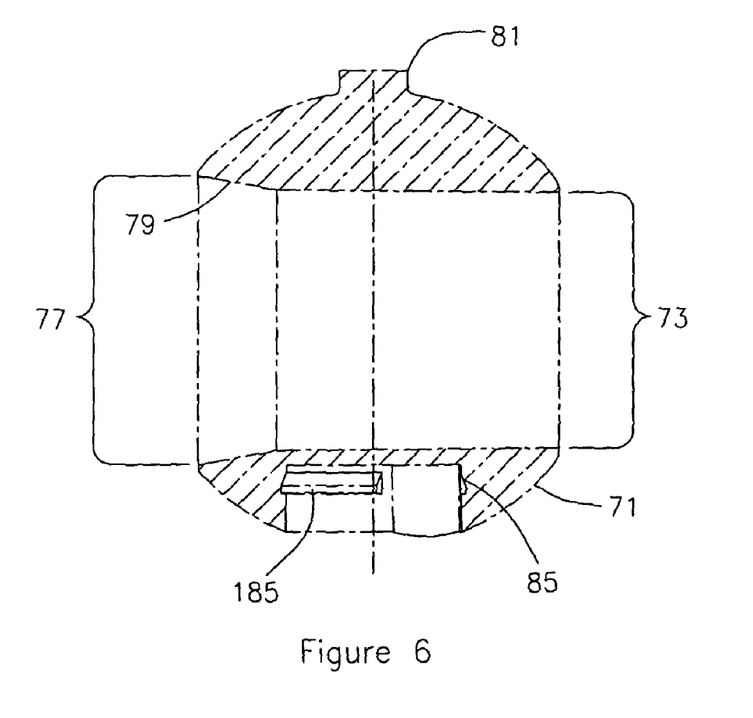
FIG. 6 is a top elevated perspective section view of closing member.

FIG. 6 is a top elevated perspective section view of closing member 71. Closing member 71 is substantially spherical, yet includes a lumened cylindrical waste passage 73. Rotation pin 81 is cylindrical and allows for seating of the closing member and turning on a single axis. The one end 77 of cylindrical waste passage is radiused to include an angled opening portion 79 to facilitate passage of waste (not shown) and subsequent cleaning. This feature is also used to align the collection manifold (not shown). Closing member handle (not shown) is locked into position by closing member handle shaft locking tabs (not shown) which seat into closing member locking tab indentations 85, 185. The angled opening portion 79 also improves passage of materials through radiused surface 150 at the seal interface (not shown) resulting in reduced 'sticktion' and closing member turning properties.

Figure 7:
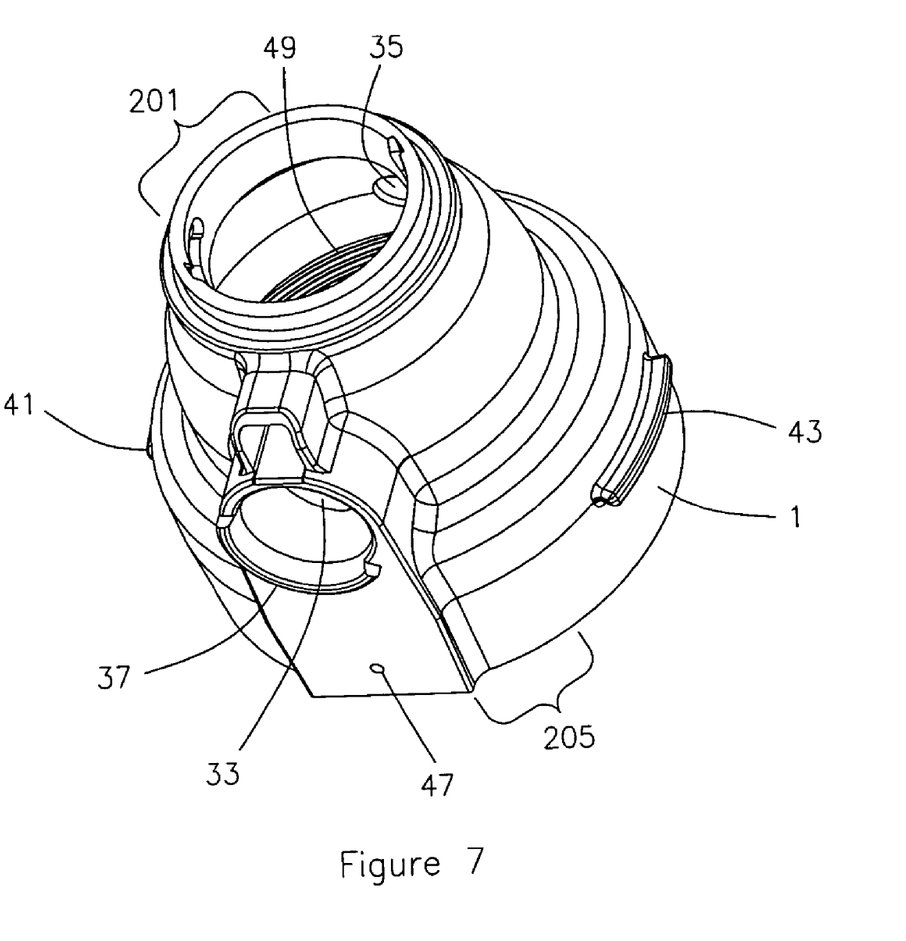
FIG. 7 is a top perspective view of housing 1.

FIG. 7 is a top perspective view of housing 1. Housing 1 encloses the internal workings of the assembled apparatus and provides ports 201, 205 for biological waste ingress and egress. Starting from the biological materials intake end 205 and working towards the biological materials removal end 201, the apparatus provides for secure storage of biological materials through the connection of a receptacle (not shown) with the apparatus. Housing 1 also has exterior flanges 41, 43 to facilitate positioning the apparatus with other devices. Housing 1 also has indentation 47 to guide placement of locking screw (not shown) to align housing 1 with fluid container (not shown) attached to intake end 205. On the exterior of housing 1, handle orifice 33 has a semi circumferential raised ridge 37 to limit the range of rotation of closing member handle (not shown). Turning now to the inside of the device, housing 1 expands to allow for insertion of closing member (not shown). Positioning of closing member (not shown) inside housing 1 is determined by the location of optional rotation pin indentation 35, which is centered across from handle orifice 33. Inside housing 1, threaded grooves 49 provide for insertion and tightening of closing member seating ring (not shown).

Figure 8:
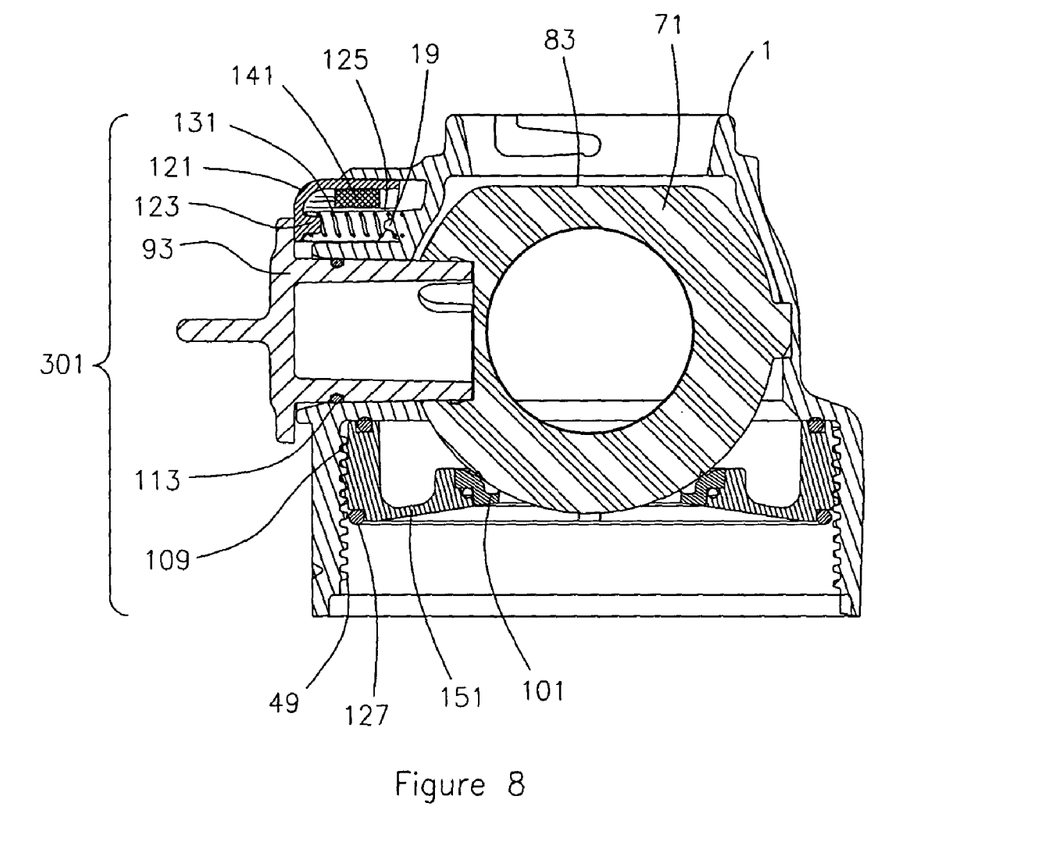
FIG. 8 is a top elevated perspective section view of the assembled apparatus.

FIG. 8 is a top elevated perspective section view of the assembled apparatus 301 when it is in the 'closed' position, with flat face 83 rotated to prevent passage of contained materials (not shown). FIG. 8 shows housing 1 assembled with closing member 71 and closing member handle 93. Because closing member 71 is in the 'closed' orientation, position of closing member handle 93 is locked into place by handle locking button 121. Button 121 returns to position by the tension provided by spring 131. Leaks are prevented through the use of closing member handle gasket 113 in conjunction with the closing member seal 101, upper seating gasket 109 and lower seating gasket 127, all of which seat into closing member seating ring 151. Housing 1 surrounds spring position post 19, and it is large enough to accommodate button 121, spring 131 and magnet 141. Closing member handle locking button 121 is seated into housing 1 once closing member handle locking button return spring 131 and magnet 141 are placed into button 121. In this assembled view, magnet 141 is positioned inside the hollow cavity of closing member handle locking button 121. Closing member handle locking button return spring 131 allows for button 121 to lock closing member handle 93 into a closed configuration. Spring 131 and magnet 141 are kept in place by spring seating column 123 and magnet rails 125 respectively. Threaded grooves 49 provide for insertion and tightening of closing member seating ring 151.

Figure 9:
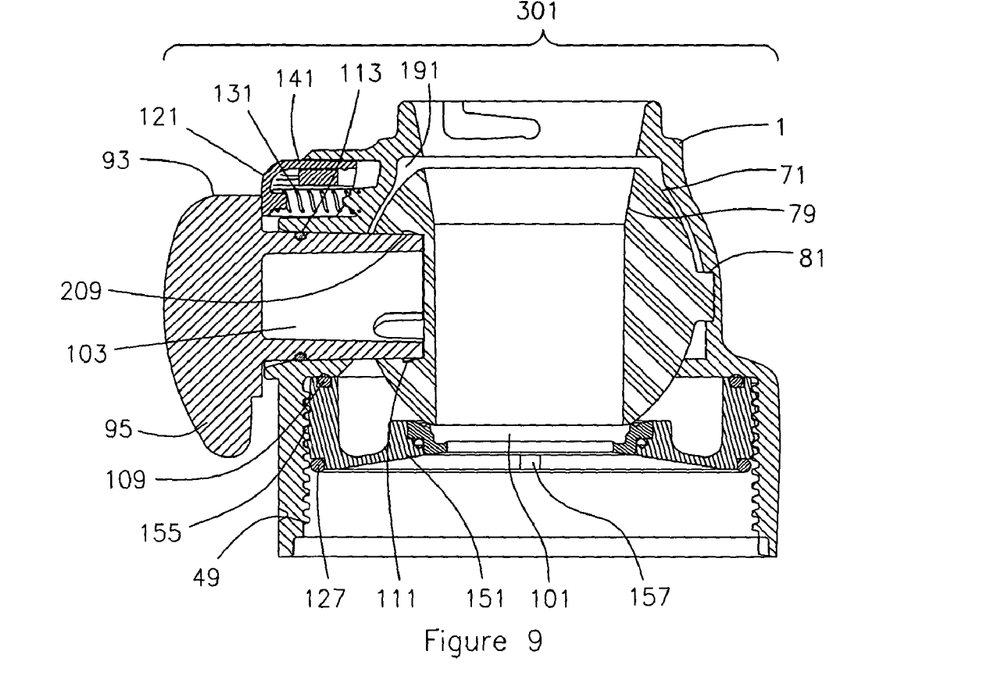
FIG. 9 is a top elevated perspective section view of the assembled apparatus.

FIG. 9 is a top elevated perspective section view of the assembled apparatus 301 when it is in the 'open' position. FIG. 9 shows housing 1 assembled with closing member 71 and closing member handle 93. Leaks are prevented through the use of closing member handle gasket 113 in conjunction with the closing member seal 101 and upper seating gasket 109, lower seating gasket 127, all of which seat into closing member seating ring 151. Inside housing 1, threaded grooves 49 provide for insertion and tightening of closing member seating ring 151. Closing member seating ring 151 is used to secure closing member 71 to housing 1. Closing member 71 is seated into housing 1 by the use of optional rotation pin 81. Optional rotation pin 81 is cylindrical and allows for seating of the closing member and turning on a single axis. Closing member handle 93 has a handle 95 for manipulation of closing member 71. Closing member handle shaft 103 is hollow and terminates with closing member handle shaft locking tabs 209, 111. Closing member handle 93 is locked into position by closing member handle shaft locking tabs 209, 111. In the pictured 'open' position, closing member 71 provides close contact with seal 101 to minimize waste leakage into apparatus during disposal. To maximize sealing, a non-reactive lubricant or grease (not shown) can also be added. Closing member seating ring 151 is threaded 155, concave and contains tightening facilitator bumps 157. FIG. 9 details how closing member 71 angled opening portion 79 is oriented to facilitate passage of waste (not shown) and positioned for subsequent cleaning which is enhanced with gap 191 between housing 1 and closing member 71. Gap 191 exists between housing 1 and closing member 71 when closing member 71 is open to allow for greater surface area cleansing of closing member 71 and related parts.

Figure 10:
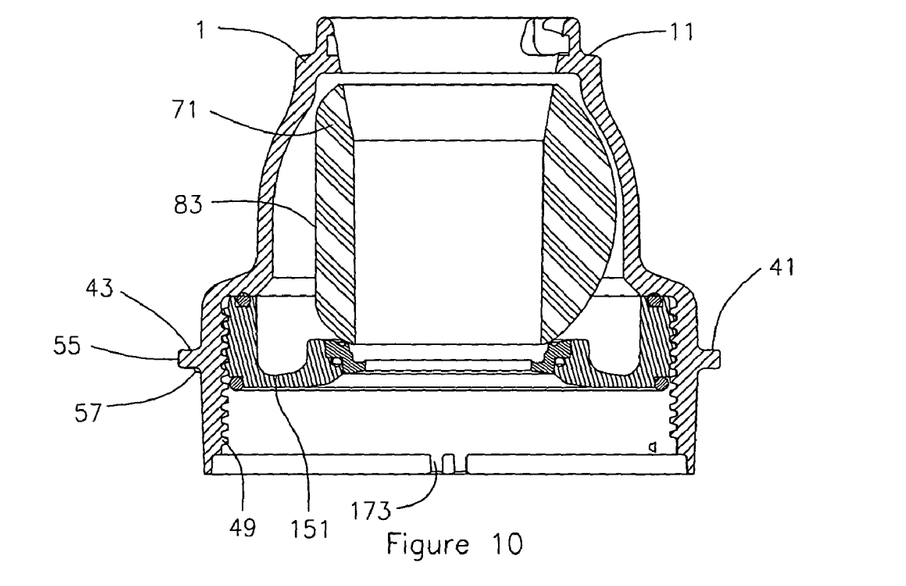
FIG. 10 is a cross sectional view of the assembled apparatus when it is in the 'open' position.

FIG. 10 is a cross sectional view of the assembled apparatus when it is in the 'open' position. FIG. 10 shows housing 1 assembled with closing member 71. Closing member 71 is substantially spherical, yet includes a flat face 83 which is rotated into position during closing member operation. In the present illustration, flat face 83 has been turned to allow for the passage of waste material from the vessel (not shown) and subsequent cleaning of the apparatus and vessel. Housing 1 also provides a ridge 11 as well as flanges 41 and 43. Flange 43 has two additional locking tabs 55, 57 to orient housing 1. Turning now to the inside of the device, housing 1 expands to allow for insertion of closing member 71. Inside housing 1, threaded grooves 49 provide for insertion and tightening of closing member seating ring 151 and abut orienting feature 173.

Figure 11:
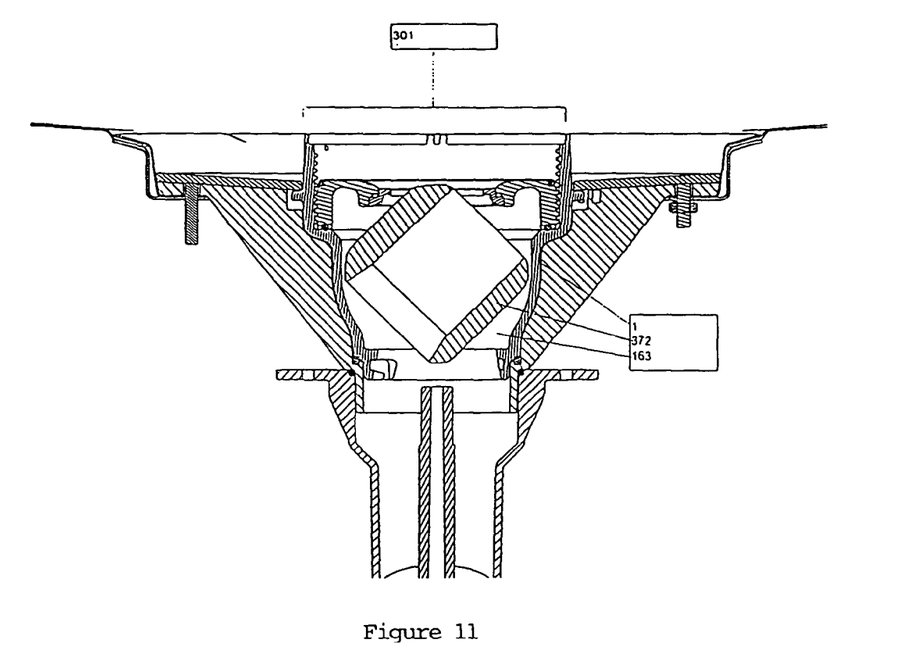
FIG. 11 is a top elevated perspective section view of the assembled apparatus incorporated into a waste station with alternate valve embodiment.

FIG. 11 is a top elevated perspective section view of the assembled apparatus 301 with alternate embodiment of closing member 371 intermediately between an open and closed position. The irrigation cleaning chamber 163 is more accessible to cleaning and irrigation fluids when in this position. It needs to be appreciated that apparatus 301 is designed to interface with a rotational mechanism (not shown) which can, in a specifically controlled frequency and arc, direct a stream of cleaning fluid in a desired manner based on the orientation of closing member 372. Dynamically opening and closing the member allows access to the irrigation chamber to thoroughly clean all surfaces of closing member 372 and the interior of housing 1. This automated rotation can take place in a sealed path connection with a disposal station allowing thorough cleaning via jet spray and not allow overspill of contained materials (not shown) to reach the outside environment. Moreover, this orientation can also direct the spray of cleaning fluid to specific locations on an attached waste vessel (not shown) when attached.

Figure 12:
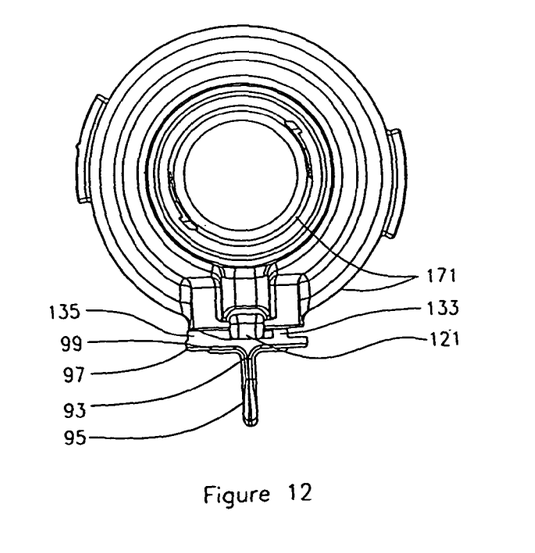
FIG. 12 is a plan view of the assembled apparatus when it is in the 'open' position.

FIG. 12 is a plan view of the assembled apparatus when it is in the 'open' position. FIG. 11 shows housing 1 assembled with closing member 71 and closing member handle 93. The external surface of closing member handle 93 is made up of handle 95 connected to handle face 97 with handle face raised feature 99. From this view locking tab open stop 133 and locking tab closed stop 135 can be seen. Locking tab closed stop 135 automatically secures button 121 and prevents motion of the closing member 71 until button 121 is physically depressed, and prevents rotation beyond a specified angle, as well as preventing rotation from the closed position unless button 121 is depressed.

Figure 13:
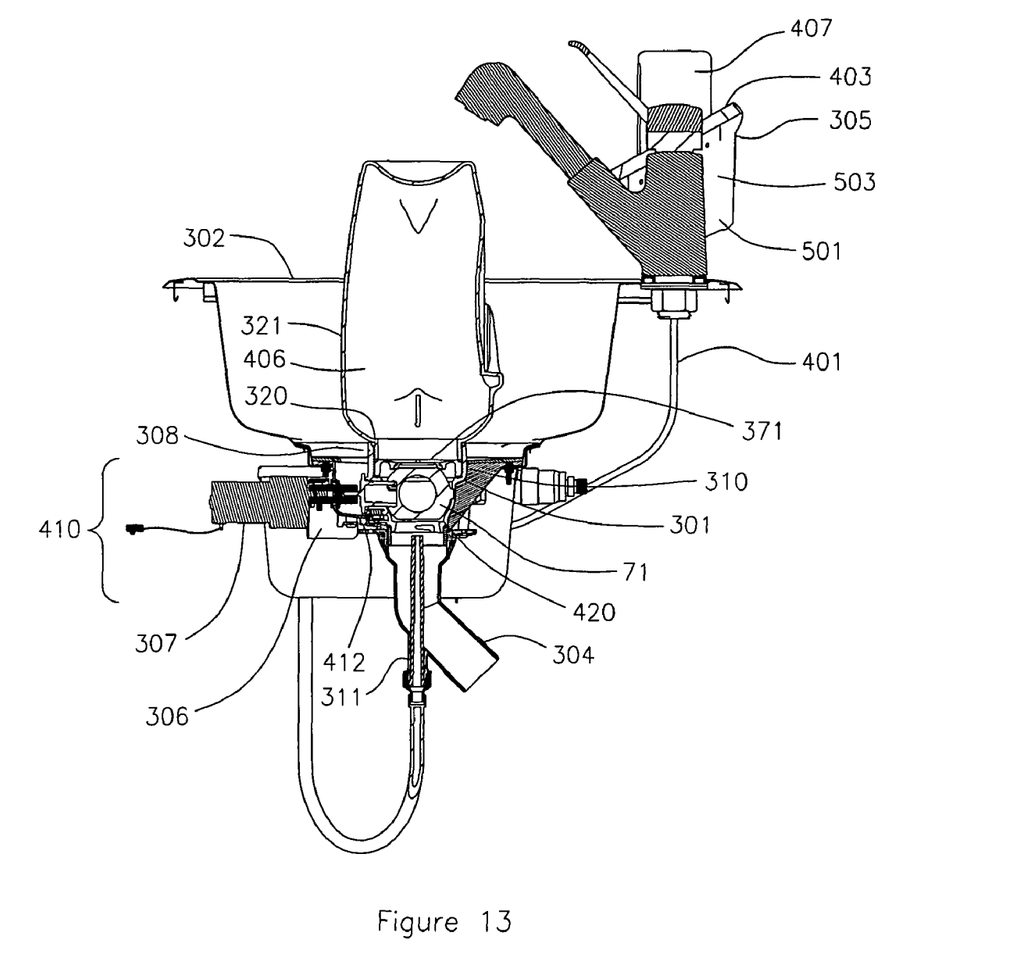
FIG. 13 is a top elevated perspective section view of the assembled apparatus incorporated into a waste station.

FIG. 13 is a side view of the assembled apparatus 301 connected to waste vessel 321 containing medical waste 406 incorporated into a fully 'smart' or controlled gateway waste disposal system incorporated with controller 305 and motor 307. Assembled apparatus 301 in conjunction with vessel 321 links sink 302 with sewer line 304. Sensors 306, 308 and 310 sense signals from transmitters 320 and 412. The signals or the absence thereof is communicated to control mechanism 305 which operates motor 307, cleaning water source 401, cleaning and disinfectant solution source 407 in conjunction with user interface 403. Sensors and transmitters 306, 308,

310, 320 and 412 can be magnetic, radio frequency devices or purely mechanical. In a Radio Frequency embodiment sensors and transmitters 306, 308, 310, 320 and 412 can provide and optionally store device specific information such as device cycle count or estimated cycles available before replacement. When closing member 71 is turned by motor 307 into the 'closed' position as depicted, waste materials will not flow to sewer output 304, but when closing member 71 is rotated into the open position cleaning fluid from cleaning fluid reservoir 407 can be dispensed by cleaning pipe 311 and clean the internal components of apparatus 301 in conjunction with vessel 321 but is prevented from escaping because of the internal sealing at 420. Drainage of biological waste 406 or cleaning fluid (not shown) is facilitated through vent (not shown). Vent (not shown) can be boosted by way of vacuum assistance. Ingress of cleaning fluid (not shown) or egress of waste material 406 is controlled by controller 305, which controls cleaning time, cleaning fluid amount and cycling of closing member 71. Based on varying each of these factors, controller 305 can regulate the position of cleaning fluid both within apparatus 301 as well as waste vessel 321 due to specific orientation of closing member 71. Transmitter 320 on waste vessel 321 relays its characteristics to controller 305 to identify the contents of waste vessel as well as other information including vessel use cycle count. Based on the identity of sensor 320 on waste vessel 321, controller 305 varies cleaning parameters such as wash time, cleaning fluid amount and number of times to cycle closing member 71 open and closed to facilitate cleaning. Since the type and consistency of contents of waste vessel 321 is identified by the particular type of transmitter 320 detected by controller 305 cleaning times can be made longer or shorter, or vary the specific type of cleaning fluid (not shown) as called for by controller 305. In addition, a use cycle count is also made which can prevent subsequent use of vessel 321 if it has exceeded a preprogrammed standard value. During cleaning, waste vessel 321 is inserted into apparatus 301 by inversion, but contents of vessel 301 are contained due to the presence of locking cap 371 which prevents egress of contents until waste vessel 321 is fully seated into apparatus 301 by rotation, causing closing member 71 to open. Proper seating is confirmed to the user through tactile feedback which occurs when insertion rotation is complete. Once closing member 71 is opened, contents of waste vessel 321 are emptied and waste vessel 321 is then cleaned while preventing spillage or undesired discharge of the contents of waste vessel 321 anywhere but through the internal surface of valve manifold housing assembly 410. In a foreseen variant of locking cap 371, locking cap 371 can only be intentionally locked or unlocked via a corresponding locking element.

The physical conformation of waste vessel 321 is specifically designed to prevent pooling or retention of contaminated waste matter. In a foreseen variant, the estimated life cycle of apparatus 301 can be calculated by controller 305 and varied based upon the different types of waste material encountered as identified by transmitter 320. Apparatus 301 can also be operated with stopper (not shown) which contains sensor (not shown) which prevents communication between the sink 302 and the sewer channel 304. This apparatus allows the sink to be used in its normal function and will permit the operator, via the user interface, to clean and disinfect the cleaning and sewer channel 304. It is understood that connections between controller 305 and sensors and transmitters 306, 308, 310, 320 and 412 could be wireless as well as wired.

Controller 305 incorporates CPU 501, and memory 503 which allow for automated cleaning functions to take place based upon input from sensor 320. Automated cleaning routines include the ability to target the spray of cleaning fluid based upon the orientation of closing member 71. Cleaning routines can be proportionally varied based upon the age of the vessel and content type as well as by vessel color if an optical sensor to optically detect vessel color properties is integrated into the system.

Cleaning controlled by controller 305 can vary wash functions (or prevent wash functions on devices which have exhausted their product cycle) based on wash time, rinse time, quantity of cleaning fluid, and allow for the incorporation of cleaning protocol standards should they become required by government entities such as the FDA.

Memory 503 can also retain information regarding specific vessels based upon input from sensors and transmitters 306, 308, 310, 320 and 412. This information includes type of vessel, number of times a particular vessel has been cleaned, and parameters for cleaning maximums. In one embodiment, the vessel cleaning maximum is not only a function of the number of times a vessel has been cleaned, but also calculates a 'wear' component. An example of this would be if a vessel was only 'cold sterilized' for one type of contents then 'hot sterilized' to account for another type of contents, the overall calculated lifespan of the vessel could be reduced to account for the greater 'wear and tear' of the heat sterilization.

While the described system and method incorporates data transfer between vessels and the waste receptacle system, data transfer may alternately take place by way of remote sensors (not shown) reading vessel 321 properties which have not been docked with apparatus 301.

Information as herein shown and described in detail is fully capable of attaining the above-described object of the invention, the presently preferred embodiment of the invention, and is, thus, representative of the subject matter which is broadly contemplated by the present invention. The scope of the present invention fully encompasses other embodiments which may become obvious to those skilled in the art, and is to be limited, accordingly, by nothing other than the appended claims, wherein reference to an element in the singular is not intended to mean "one and only one" unless explicitly so stated, but rather "one or more." All structural and functional equivalents to the elements of the above-described preferred embodiment and additional embodiments that are known to those of ordinary skill in the art are hereby expressly incorporated by reference. And are intended to be encompassed by the present claims. Moreover, no requirement exists for a device or method to address each and every problem sought to be resolved by the present invention, for such to be encompassed by the present claims. Furthermore, no element, component, or method step in the present disclosure is intended to be dedicated to the public regardless of whether the element, component, or method step is explicitly recited in the claims. However, it should be readily apparent to those of ordinary skill in the art that various changes and modifications in form, apparatus material, and fabrication material detail may be made without departing from the spirit and scope of the inventions as set forth in the appended claims. No claim herein is to be construed under the provisions of 35 U.S.C. 112, sixth paragraph, unless the element is expressly recited using the phrase "means for."

INDUSTRIAL APPLICABILITY

The claimed invention has industrial applicability in the medical field for safe and secure disposal of medical waste. Moreover, the claimed invention also has industrial applicability in the biological research field where safe containment and disposal of biological and organic materials is also useful.

We claim:

1. A self cleansing biological fluid waste collection system for connecting a waste vessel to a waste removal station for removal of biological fluid from the waste vessel and cleaning of the waste vessel, the system comprising:
   a) a waste vessel with locking cap,
   b) wherein said waste vessel with locking cap connects to a disposal apparatus, wherein the locking cap prevents opening of the waste vessel when not connected to the disposal apparatus,
   c) wherein the locking cap is configure to require an unlocking manipulation separate from an opening manipulation of the locking cap, wherein the opening manipulation opens the waste vessel;
   d) wherein the disposal apparatus interoperates with the locking mechanism to unlock the locking mechanism once the waste vessel is properly seated to the disposal apparatus;
   e) wherein said waste vessel is configured to be opened and closed by a motor activated by a controller, and may also be opened and closed manually,
   f) wherein said controller controls the release of cleaning agents through a cleaning pipe to clean said waste vessel,
   g) whereby input from a waste vessel ID wherein information comprising information concerning cleaning cycles, is structurally encoded in the waste vessel ID and information is transferred from the waste vessel to a sensor to be processed by the controller whereby transmission of information from the waste vessel ID is independent of the operator, and the information structurally encoded in the waste vessel ID is recorded so the cleaning cycles of the waste vessel are tracked for purposes of disposal and replacement of the waste vessel after a prescribed number of cleaning cycles where the number of cleaning cycles are greater than one.

2. The biological waste collection system of claim 1, wherein said controller is connected to a user interface device.

3. The biological waste collection system for connecting a waste vessel to a waste removal station of claim 2, wherein said controller is configured to control the cleaning of said vessel with cleaning routines based on input from waste vessel ID characteristics.

4. The biological waste collection system for connecting a waste vessel to a waste removal station of claim 3, wherein the position and orientation of the waste vessel is determined by measurements taken of at least one sensor.

5. The biological waste collection system for connecting a waste vessel to a waste removal station of claim 4, wherein said waste vessel additionally comprises one or more identifying components in the waste vessel ID for identifying vessel characteristics to said controller.

6. The biological waste collection system for connecting a waste vessel to a waste removal station of claim 5, wherein said identifying components store vessel use frequency and contents information.

7. The biological waste collection system for connecting a waste vessel to a waste removal station of claim 6, wherein said sensor is selected from the group consisting of magnetic, Radio Frequency ID or mechanical.

8. The biological waste collection system for connecting a waste vessel to a waste removal station of claim 7, wherein said controller additionally comprises one or more central processing units and memory units.

9. The biological waste collection system for connecting a waste vessel to a waste removal station of claim 8, additionally comprising a stopper element.

10. The biological waste collection system of claim 9, wherein said controller monitors vessel presence, absence and contents by type.

11. The biological waste collection system of claim 10, wherein said controller monitors vessel use frequency and is configurable to prevent use of said vessel when a predetermined value is reached.

12. The biological waste collection system of claim 11, wherein said vessel additionally comprises an identifying component with memory element.

* * * * *